(12) United States Patent
Tanaka

(10) Patent No.: US 8,211,713 B2
(45) Date of Patent: Jul. 3, 2012

(54) METHOD FOR DETERMINING AN ANALYTE IN A SAMPLE BY AGGLUTINATION

(75) Inventor: Mutsumi Tanaka, Ibaraki (JP)

(73) Assignee: Alfresa Pharma Corporation, Osaka (JP)

( * ) Notice: Subject to any disclaimer, the term of this patent is extended or adjusted under 35 U.S.C. 154(b) by 160 days.

(21) Appl. No.: 12/298,180

(22) PCT Filed: Mar. 9, 2007

(86) PCT No.: PCT/JP2007/055317
§ 371 (c)(1),
(2), (4) Date: Oct. 23, 2008

(87) PCT Pub. No.: WO2007/125689
PCT Pub. Date: Nov. 8, 2007

(65) Prior Publication Data
US 2009/0098661 A1    Apr. 16, 2009

(30) Foreign Application Priority Data

Apr. 28, 2006  (JP) ................................ 2006-126564

(51) Int. Cl.
*G01N 33/53*    (2006.01)

(52) U.S. Cl. ...... 436/518; 435/7.1; 435/7.94; 422/82.05

(58) Field of Classification Search ................... 435/7.1, 435/7.94
See application file for complete search history.

(56) References Cited

U.S. PATENT DOCUMENTS

| 4,189,466 A | * | 2/1980 | Ainis et al. ................... | 435/7.32 |
| 2004/0161863 A1 | * | 8/2004 | Brock et al. .................. | 436/536 |
| 2006/0172351 A1 | * | 8/2006 | Sumida et al. ............... | 435/7.23 |

FOREIGN PATENT DOCUMENTS

| JP | 54032618 A | 3/1979 |
| JP | 2247564 A | 10/1990 |
| JP | 2004325192 A | 11/2004 |
| JP | 2005283250 A | 10/2005 |
| WO | 2004077011 A2 | 9/2004 |

* cited by examiner

*Primary Examiner* — Bao Thuy L Nguyen
(74) *Attorney, Agent, or Firm* — The Webb Law Firm

(57) ABSTRACT

A method for determining an analyte in a sample, includes the steps of: (a) mixing the analyte and a first specific binding substance, the first specific binding substance being a substance that can specifically bind to the analyte; (b) adding microparticles having a second specific binding substance bound thereto to a mixture obtained in the step (a) and mixing therewith, the second specific binding substance being a substance that can specifically bind to the first specific binding substance; and (c) determining an agglutination reaction of the microparticles in a mixture obtained in the step (b).

8 Claims, 3 Drawing Sheets

METHOD FOR DETERMINING AN ANALYTE IN A SAMPLE BY AGGLUTINATION

TECHNICAL FIELD

The present invention relates to an immunoassay using microparticles having a substance bound thereto. In particular, the present invention relates to an immunoassay of a trace constituent using an antigen-antibody reaction for use mainly in the industrial, environmental, and clinical laboratory test fields, and to a reagent kit for immunoassay.

BACKGROUND ART

In recent years, automation in various types of tests such as clinical laboratory tests and reduction in the assay time thereof have been tried. As a method of these tests, an assay utilizing an immune reaction is widely used for measurement of a substance in a biological sample. Examples of the immunoassay include many methods such as RIA, EIA, immunonephelometry, latex agglutination, colloidal gold agglutination, and immunochromatography. Among such methods, the latex agglutination and the colloidal gold agglutination are capable of measurement in a homogeneous system in which the separation or washing operation of a reaction mixture is not required, and therefore suitable for automation of determination and short-time assay. In particular, colloidal gold particles have a size of 5 nm to 100 nm, which is smaller than the size of latex particles, so that colloidal gold particles can be used in an assay of a tracer substance (Japanese Laid-Open Patent Publication Nos. 2005-283250 and 2004-325192).

The main reactive component in these assays is a substance that specifically reacts with the analyte bound to the latex particles or the colloidal gold particles. This substance that specifically reacts with the analyte varies depending on the analyte, and thus it is necessary to prepare specific microparticles having such a substance bound thereto in accordance with the analyte.

However, the operation of preparing such microparticles is complicated. Furthermore, some types of substance to be bound to the microparticles may not easily bind to a carrier, may nonspecifically undergo autoagglutination even when being bound to the carrier and thus cannot be used in an assay system, or may change in the specificity or the avidity to the analyte due to binding and thus cannot be used.

SUMMARY OF THE INVENTION

It is an object of the present invention to provide an assay of a sample using an agglutination reaction of immunological microparticles and a kit for the assay, and the assay and the kit do not require any complicated operation as described above in which different substances are bound to microparticles of latex, gold colloid, or the like with respect to each of different analytes. Furthermore, it is an object of the present invention to solve even the problem in that the substance sometimes may not be suitable for binding to the microparticles as described above.

In the present invention, more convenient assay can be achieved by binding a substance that specifically recognizes a substance that specifically binds to an analyte to microparticles of latex, gold colloid, or the like, rather than binding the substance that specifically binds to the analyte to microparticles of latex, gold colloid, or the like, and using the microparticles as the main component of the agglutination reaction.

The present invention provides a method for determining an analyte in a sample, said method comprises:

(a) mixing the analyte and a first specific binding substance, the first specific binding substance being a substance that can specifically bind to the analyte;

(b) adding microparticles having a second specific binding substance bound thereto to a mixture obtained in the step (a) and mixing therewith, the second specific binding substance being a substance that can specifically bind to the first specific binding substance; and (c) determining an agglutination reaction of the microparticles in a mixture obtained in the step (b).

In one embodiment, in the step (b), an analyte-bound carrier is added simultaneously with the microparticles, the analyte-bound carrier being a carrier to which a plurality of analytes or a plurality of sites of the analytes that are recognized by the first specific binding substance are bound.

In a certain embodiment, the first specific binding substance is an antibody against the analyte.

In a further embodiment, the second specific binding substance is an antibody against the first specific binding substance, and preferably a monoclonal antibody.

In one embodiment, the microparticles are of latex or gold colloid.

The present invention further provides a reagent kit for determination, said kit comprises:

a first reagent containing a first specific binding substance that is a substance that can specifically bind to an analyte; and a second reagent containing microparticles having a second specific binding substance bound thereto, the second specific binding substance being a substance that can specifically bind to the first specific binding substance.

In an embodiment, the second reagent further contains an analyte-bound carrier that is a carrier to which a plurality of analytes or a plurality of sites of the analytes that are recognized by the first specific binding substance are bound.

In the method of the present invention, the microparticles of latex, gold colloid, or the like having the second specific binding substance bound thereto are used as the main component of the agglutination reaction, and the second specific binding substance specifically recognizes the first specific binding substance that specifically binds to the analyte. Accordingly, when a specific site recognized by the second specific binding substance to be bound to the microparticles is set to be a common region to first specific binding substances that specifically bind to analytes, for example, the Fc region of antibodies when the first specific binding substances are the antibodies or a tag region added to the first specific binding substances using a chemical or molecular biological technique, the analytes can be easily determined simply by changing the first specific binding substances (e.g., antibodies against the analytes) in accordance with the analytes. That is to say, there is no need to perform the complicated operation of binding different substances to the microparticles with respect to each of different analytes.

Furthermore, according to the present invention, the substance (the first specific binding substance) that directly binds to the analyte is not bound to the microparticles of latex, gold colloid, or the like, and this also leads to elimination of uncertainties due to binding with the microparticles, such as the change in the specificity of the first specific binding substance, the avidity of the first specific binding substance to bind to the analyte, the possibility of autoagglutination, and the change in the stability of the first specific binding substance.

BEST MODE FOR CARRYING OUT THE INVENTION

Figure 1:
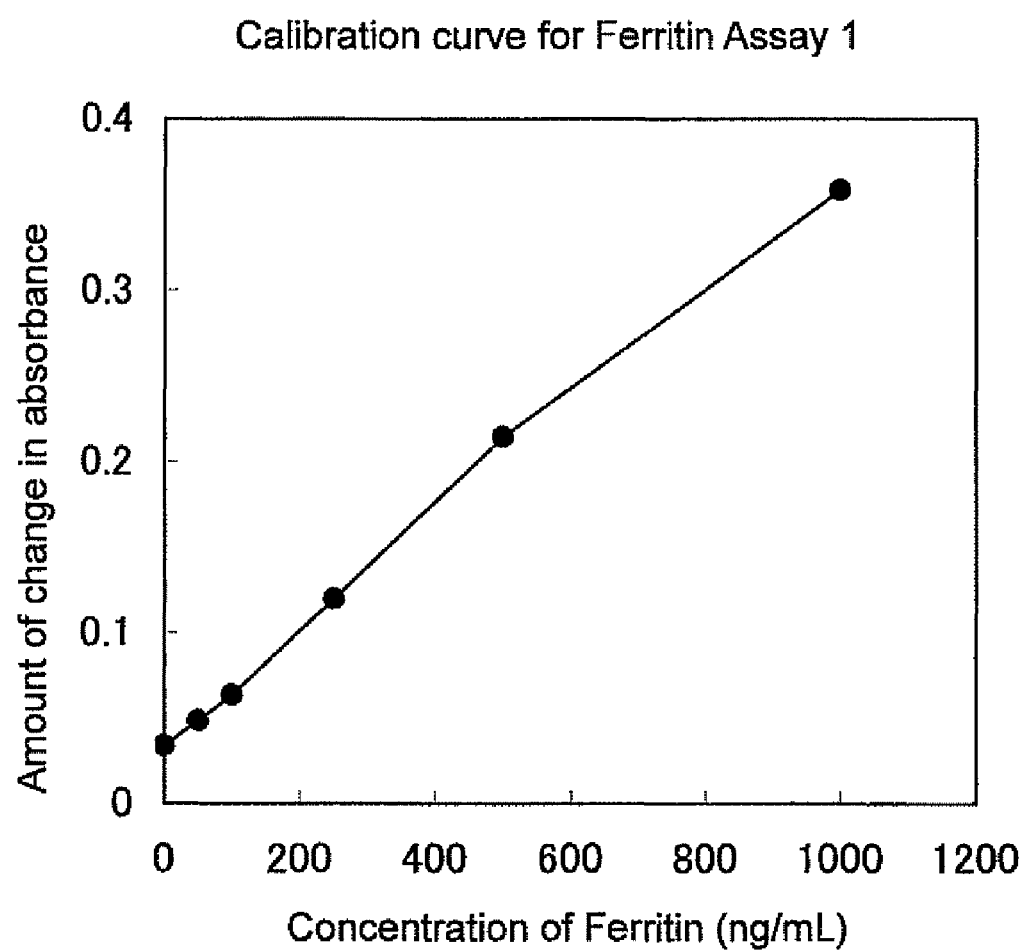
FIG. 1 is a graph showing the relationship between the concentration of ferritin and the amount of change in absorbance in Ferritin Assay 1, wherein the graph represents a calibration curve for Ferritin Assay 1.

In the present invention, examples of samples containing an analyte used in an assay include biological samples such as blood, plasma, serum, urine, feces (in suspension), cerebrospinal fluid, and ascites fluid; and those collected from the environment or extracts thereof.

The analyte is not particularly limited as long as a substance (the first specific binding substance) that specifically binds to the analyte can exist. Examples of the analyte include proteins such as albumin, hemoglobin, hemoglobin A1c, myoglobin, transferrin, lactoferrin, cystatin C, ferritin, α-fetoprotein, carcinoembryonic antigen, CA19-9, prostate-specific antigen, C-reactive protein (CRP), fibrin degradation product (FDP), pepsinogens I and II, and collagen; lipoproteins such as high-density lipoprotein, low-density lipoprotein, and very low-density lipoprotein; nucleic acids such as deoxyribonucleic acid and ribonucleic acid; enzymes such as alkaline phosphatase, lactate dehydrogenase, lipase, and amylase; immunoglobulins such as IgG, IgM, IgA, IgD, and IgE; antigens and antibodies associated with infectious diseases, such as hepatitis B virus, hepatitis C virus, human immunodeficiency virus, and *Helicobacter pylori* and antibodies thereto; drugs such as haloperidol and bromperidol; and hormones such as sex hormone.

An example of the substance (the first specific binding substance) that specifically binds to the analyte is an antibody or an antigen that can be used in an immunoassay that uses an immune reaction. For example, substances having binding affinity, such as antibodies or antigens, receptors, lectin, deoxyribonucleic acid (DNA), and ribonucleic acid (RNA), can be used. Preferably, a polyclonal antibody or a monoclonal antibody is used because these antibodies can specifically recognize the analyte and are easily recognized by the second specific binding substance that will be described in detail below. Moreover, a site recognized by the second specific binding substance (e.g., a tag) may be added to the first specific binding substance using a chemical or molecular biological technique. Such a first specific binding substance may be commercially available or may be prepared by a method commonly used by those skilled in the art in accordance with the analyte.

The substance (the second specific binding substance) that specifically binds to the substance (the first specifically binging substance) that specifically binds to the analyte is bound to microparticles. An example of the second specific binding substance is an antibody or an antigen that can be used in an immunoassay utilizing an immune reaction. Alternatively, a substance that specifically binds to a substance that specifically binds to the target to be measured can also be used. For example, substances having binding affinity, such as antibodies or antigens, receptors, lectin, deoxyribonucleic acid (DNA) and ribonucleic acid (RNA), can be used.

The second specific binding substance specifically binds to the first specific binding substance, and the binding site thereof may recognize any region present in the first specific binding substance. For example, when the first specific binding substance is an antibody, the region may be the Fc region or the V region of the antibody or a tag region or the like added to the antibody using a chemical or molecular biological technique. When the second specific binding substance is an antibody, the second specific binding substance may be a polyclonal antibody or may be a monoclonal antibody. Such a second specific binding substance may be commercially available or may be prepared by a method commonly used by those skilled in the art in accordance with the first specific binding substance.

In the present invention, the microparticles to which the second specific binding substance is bound can be any microparticles that can be used for an immunoassay reagent. Latex and metal colloid are preferably used. In the case of metal colloid, gold colloid is preferable in view of generally ease to use. Commercially available colloidal gold particles may be used, or colloidal gold particles may be prepared by a method commonly used by those skilled in the art (e.g., a method of reducing chloroauric acid with sodium citrate). The particle size of the colloidal gold particles is usually in the range of 10 nm to 100 nm, preferably in the range of 30 nm to 60 nm.

The colloidal gold particles (hereinafter sometimes referred to as the bound colloidal gold particles) having the second specific binding substance bound thereto used in the method of the present invention can be prepared, for example, in the following manner. First, usually 0.1 mg to 100 mg, preferably 1 mg to 10 mg, of the second specific binding substance (e.g., an antibody) is added to 1 L of a colloidal solution containing gold particles (having an absorbance at 540 nm of about 2.0), and the mixture is stirred under refrigeration or at room temperature for 5 minutes to 24 hours. Then, the mixture is subjected to blocking with bovine serum albumin (BSA) or the like and centrifuged, and thus the desired bound colloidal gold particles can be obtained. The obtained microparticles are dispersed in a buffer solution to attain a concentration required for assay. The pH of the buffer solution is preferably 5 to 9, and the concentration thereof is preferably 1 to 100 mM. For example, a phosphate buffer solution, a Tris-HCl buffer solution, a succinate buffer solution, or a Good's buffer solution such as glycylglycine, MES (2-(N-morpholino)ethanesulfonic acid), HEPES (N-2-hydroxyethyl-piperazine-N'-ethanesulfonic acid), TES (N-tris (hydroxymethyl)methyl-2-aminoethanesulfonic acid), MOPS (3-(N-morpholino)propanesulfonic acid), PIPES (piperazine-1,4-bis(2-ethanesulfonic acid)), or Bis-Tris (bis (2-hydroxyethyl)iminotris (hydroxymethyl)methane) is preferably used as the buffer solution.

The buffer solution may contain additives, for example, sugars and sugar alcohols, albumin, salts such as sodium chloride, and antiseptics, as necessary. Examples of the sugars and sugar alcohols include glucose, mannose, saccharose, lactose, maltose, mannitol, and sorbitol. The concentration thereof is preferably 0.01 to 10 w/v %. As for the albumin, bovine serum albumin (BSA) is preferably used, and the concentration thereof is preferably 0.001 to 1 w/v %. As for the antiseptics, sodium azide is preferably used, and the concentration thereof is preferably 0.01 to 0.5 w/v %. Examples of other additives include Tween 20, polyethylene glycol lauryl ether, 5-bromosalicylic acid, sodium salicylate, sodium benzoate, sodium benzenesulfonate, phenol, and thymol.

In the present invention, when necessary, a carrier to which a plurality of analytes or a plurality of sites of the analytes (i.e., portions of the analytes) that are recognized by the first specifically binging substance are bound is allowed to coexist with the microparticles having the second specifically binging substance bound thereto. The carrier to which a plurality of analytes or portions thereof are to be bound is suitably selected from albumin, hemocyanin, thyroglobulin, fibrinogen, enzyme, and the like derived from various animals. In the present invention, bovine serum albumin (BSA) is preferably used. Preferably, about 4 to 40 analytes or portions thereof are bound per molecule of the carrier.

The binding between the analytes or portions thereof and the carrier can be performed by a method commonly used by those skilled in the art. According to such a binding method, a chemical bond is formed between the analytes or portions thereof and the carrier directly or via a binder by using a functional group, such as an amino group, a carboxyl group, or a thiol group, that is present in the analytes or portions thereof. Depending on the structure of the analytes or portions thereof, various methods are known (Laboratory Techniques in Biochemistry and Molecular Biology (Seikagaku Jikken Hou) 11, Enzyme Immunoassay, written by P. Tijssen, edited by Eiji Ishikawa, p. 252, 1989, Tokyo Kagaku Dozin Co., Ltd.). Examples of a reagent for forming a chemical bond include an acylating agent and an alkylating agent. Preferably, N-hydroxysuccinimido ester which may be obtained by activating a carboxyl group, maleimides which may be used under weakly alkaline conditions, or the like is used.

In the binding reaction between the analyte and the first specific binding substance and the agglutination reaction between the bound matter and the second specific binding substance, reaction conditions such as the reaction temperature, the pH, the type of the buffer solution, the type of the coexistent salt and the concentration thereof, and the other coexistent substances are the same as those in conventional immunological reactions. For example, in order to promote the reactions, a water-soluble polymer such as polyethylene glycol, polyvinyl alcohol, dextran, or sodium chondroitin sulfate may be added to the reaction system, as is commonly performed.

In the present invention, the method for determining an analyte in a sample includes the steps of:

(a) mixing the analyte and the first specific binding substance, the first specific binding substance being a substance that can specifically bind to the analyte;

(b) adding microparticles having the second specific binding substance bound thereto to a mixture obtained in the step (a) and mixing therewith, the second specific binding substance being a substance that can specifically bind to the first specific binding substance; and (c) determining the agglutination reaction of the microparticles in a mixture obtained in the step (b).

In this method, when the analyte can bind with a plurality of first specific binding substances, the analyte and the substance (the first specific binding substance) that specifically binds to the analyte are reacted to form a complex in the step (a), the complex is then, in the step (b), allowed to react with the microparticles (hereinafter sometimes referred to as the bound microparticles) of latex, gold colloid, or the like having the substance (the second specific binding substance) that recognizes the substance that specifically binds to the analyte bound thereto, thereby causing an agglutination reaction, and the extent of the agglutination reaction is mechanically measured.

For example, the method of the present invention is performed in the following manner: a sample containing an analyte or a diluted liquid obtained by appropriately diluting this sample with a buffer solution or the like is mixed to form a complex with the first specific binding substance that specifically binds to the analyte; bound microparticles obtained in the above-described manner are then added to a reaction mixture containing the complex and are mixed therewith; the complex is thus reacted with the bound microparticles to cause an agglutination reaction. When gold colloid is used as the microparticles, a change in absorbance at a predetermined wavelength due to this agglutination reaction is determined. The amount of the analyte in the sample can be easily found by applying the results of the determination to a calibration curve created beforehand. The calibration curve represents the relationship between the change in the absorbance due to the colloidal gold agglutination reaction and the amount of the analyte. It should be noted that a qualitative analysis and a semi-quantitative analysis can also be performed, in which the sample is determined as negative when the change in the absorbance is less than a certain value and as positive when the change in the absorbance is not less than the certain value.

When gold colloid is used, both a single wavelength measurement and a dual wavelength measurement may be used to determine the change in the absorbance after the start of the reaction. When the dual wavelength measurement is used, the change in the absorbance is determined at the first wavelength of 610 nm to 800 nm, preferably 630 nm to 750 nm, and the second wavelength of 360 nm to 580 nm, preferably 500 nm to 550 nm. When the single wavelength measurement is used, the change in the absorbance can be determined at a wavelength in the wavelength region of either one of the first wavelength or the second wavelength used in the above-described dual wavelength measurement. In the method of the present invention, the change in the absorbance refers to values obtained by the two measurement methods described below, and either of the values can be used:

(1) the absorbance of the reaction mixture is measured twice at an appropriate interval after the start of the reaction, and the difference between the two measured values is used as the change in the absorbance; or (2) the absorbance of the reaction mixture is continuously measured after the start of the reaction, and the rate of change in the absorbance per unit time (in some cases, the maximum rate of change) is used as the change in the absorbance.

A spectrophotometer, a microplate reader, a biochemical automatic analyzer, and the like can be used in the above-described measurement. In particular, a number of samples can be determined in a short period of time by applying the method of the present invention to the measurement with the biochemical automatic analyzer.

Alternatively, in the method of the present invention, when the analyte binds with the first specific binding substance in a ratio of 1:1, the analyte and the substance (the first specific binding substance) that specifically binds to the analyte are reacted to form a complex in the step (a). In the step (b), the complex is then allowed to react with the bound microparticles in the presence of an analyte-bound carrier to which a plurality of analytes or a plurality of sites of the analytes that are recognized by the first specific binding substance are bound. Thus, an excess of the first specific binding substance that could not react in an analyte concentration-dependent manner in the step (a) binds to the analyte-bound carrier to form a complex in the step (b), and this complex further binds to the second specific binding substance bound to the bound microparticles and causes agglutination. This agglutination reaction is dependent on the amount of the first specific binding substance that is present after the step (a) and that does not bind to the analyte. This amount is defined by the amount of the analyte at the time of the reaction in the step (a), so that the amount of the analyte can be determined by mechanically measuring the extent of the agglutination reaction.

According to the present invention, a reagent kit for determination for use in the method of the present invention is provided. This kit includes a first reagent containing the first specific binding substance that is the substance that can specifically bind to the analyte; and a second reagent containing the microparticles having the second specific binding substance bound thereto. When necessary, the second reagent contains the analyte-bound carrier to which a plurality of analytes or a plurality of sites of the analytes that are recognized by the first specific binding substance are bound.

The above described reagents may be provided in any form, and preferably are provided in a state where the reagents are individually sealed and packaged. The above-described kit may include a reference standard of the analyte for use in creation of a calibration curve, a buffer solution in which each substance is dissolved at the time of use in order to prepare a solution having an appropriate concentration, instructions for use of the kit, and the like.

EXAMPLES

Hereinafter, the present invention will be described even more specifically by way of examples. However, it is to be understood that the present invention is not limited by the examples.

Example 1

Preparation of Gold Colloidal Solution

First, 2 mL of a 10 w/v % chloroauric acid solution was added to 1 L of distilled water at 95° C. under stirring, and after one minute, 10 mL of a 2 w/v % sodium citrate solution was added thereto. The resulting mixture was stirred for further 20 minutes and then cooled to 30° C. After cooling, the pH was adjusted to 7.1 with 0.1 w/v % potassium carbonate.

Example 2

Preparation of Rat Anti-Mouse IgG Monoclonal Antibody-Bound Colloidal Gold Reagent First, a rat anti-mouse IgG monoclonal antibody (Production of Antibodies, Reagents for Immunology and Services) was diluted with 10 mM HEPES (pH 7.1) containing 0.05 w/v % sodium azide to a concentration of 50 µg/mL. Then, 100 mL of this liquid was added to about 1 L of the colloidal gold solution prepared in Example 1, and the mixture was stirred under refrigeration for 2 hours. To this mixture, 110 mL of 10 mM HEPES (pH 7.1) containing 5.46 w/v % mannitol, 0.5 w/v % BSA, and 0.05 w/v % sodium azide was added, and the resulting mixture was stirred at 37° C. for 90 minutes. The mixture was centrifuged at 8000 rpm for 40 minutes to remove the supernatant. Then, about 1 L of 5 mM HEPES (pH 7.5) containing 3 w/v % mannitol, 0.1 w/v % BSA, and 0.05 w/v % sodium azide (solution A) was added to the mixture, and the antibody-bound gold colloid was dispersed. Thereafter, centrifugation was performed at 8000 rpm for 40 minutes to remove the supernatant. Then, the solution A was added to disperse the antibody-bound gold colloid so that the total amount of the resulting solution was 70 mL. Thus, a rat anti-mouse IgG monoclonal antibody-bound colloidal gold solution was prepared.

Then, 280 mL of solution A was added to 70 mL of the rat anti-mouse IgG monoclonal antibody-bound colloidal gold solution to prepare a rat anti-mouse IgG monoclonal antibody-bound colloidal gold reagent.

Example 3

Preparation of First Reagent for Ferritin Assay 1

A first reagent for Ferritin Assay 1 was prepared by adding 1.6 µg/mL of a mouse IgG anti-human ferritin antibody (Biogenesis) and about 1.0 to 2.5 w/v % of polyethylene glycol serving as a reaction accelerator to a solution of 0.2 M PIPES (pH 6.5) containing 1.0 w/v % sodium chloride, 0.5 w/v % EDTA, and 0.35 w/v % polyoxyethylene lauryl ether (solution B).

Example 4

Ferritin Assay 1

In this example, the first reagent for Ferritin Assay 1 prepared in Example 3 was used as the first reagent, and the rat anti-mouse IgG monoclonal antibody-bound gold colloidal reagent prepared in Example 2 was used as the second reagent. Solutions prepared by dissolving human ferritin in a 0.05 M HEPES solution (pH 7.4) containing 3 w/v % bovine serum albumin (solution C) at the concentrations of 0, 50, 100, 250, 500, and 1000 ng/mL, respectively, were used as standard solutions. The standard solutions were determined using a determination method that will be described below, and a calibration curve was created. Then, control serums 1, 2, and 3 manufactured by Bio-Rad Laboratories, Inc., were determined in the same manner.

Determination method: First, 160 µL of the first reagent was added to 10 µL of a sample, and the mixture was warmed at 37° C. for about 5 minutes. After warming, 80 µL of the second reagent was added and allowed to react at 37° C., and the amount of change in absorbance was measured by a Hitachi 7070 automatic analyzer at photometric points from 18 to 31 at wavelengths of 505 nm and 660 nm. FIG. 1 shows the calibration curve, and Table 1 shows the results of the determination of the control serums 1, 2, and 3.

TABLE 1

| Control serum (Indicated value: ng/mL) | Ferritin measured value (ng/mL) | |
| --- | --- | --- |
| | First measurment | Second measurement |
| LEVEL 1 (19-33) | 22 | 18 |
| LEVEL 2 (104-185) | 124 | 125 |
| LEVEL 3 (207-369) | 255 | 248 |

As shown by the calibration curve in FIG. 1, the amount of change in absorbance due to the agglutination reaction was increased depending on the concentration of the analyte ferritin. In other words, it can be found that the amount of ferritin, which is the analyte contained in the sample, can be quantified by measuring the amount of change in absorbance due to the agglutination reaction and performing a comparison with the calibration curve. The results of the determination of the ferritin concentration shown in Table 1 were within the ranges of the indicated values for the amount of ferritin in the control serums, and the accuracy of the present determination method was confirmed.

Example 5

Preparation of Mouse Anti-Rabbit IgG-Fc Monoclonal Antibody-Bound Colloidal Gold Reagent First, a mouse anti-rabbit IgG-Fc monoclonal antibody (Biogenesis) was diluted with 10 mM HEPES (pH 7.1) containing 0.05 w/v % sodium azide to a concentration of 50 µg/mL. Next, 100 mL of this liquid was added to about 1 L of a colloidal gold solution as prepared in Example 1, and the mixture was stirred under refrigeration for 2 hours. Then, about 1 L of solution A was added to disperse the antibody-bound gold colloid. Thereafter, centrifugation was performed at 8000 rpm for 40 minutes to remove the supernatant, and the antibody-bound gold colloid was dispersed using solution A so that the total amount of the resulting solution was 70 mL. Thus, a mouse anti-rabbit IgG-Fc monoclonal antibody-bound gold colloidal solution was prepared.

Then, 280 mL of solution A was added to 70 mL of the mouse anti-rabbit IgG-Fc monoclonal antibody-bound colloidal gold solution to prepare a mouse anti-rabbit IgG-Fc monoclonal antibody-bound colloidal gold reagent.

Example 6

Preparation of First Reagent for Ferritin Assay 2

A first reagent for Ferritin Assay 2 was prepared by adding 0.25 µg/mL of a rabbit anti-human ferritin polyclonal antibody (DakoCytomation A/S) and about 1.0 to 2.5 w/v % of polyethylene glycol serving as a reaction accelerator to the solution B as described above.

Example 7

Ferritin Assay 2

In this example, the first reagent for Ferritin Assay 2 prepared in Example 6 was used as the first reagent, and the mouse anti-rabbit IgG-Fc monoclonal antibody-bound colloidal gold reagent prepared in Example 5 was used as the second reagent. Solutions prepared by dissolving human ferritin in the solution C at the concentrations of 0, 50, 100, 250, 500, and 1000 ng/mL, respectively, were used as standard solutions. The standard solutions were determined using a determination method that will be described below, and a calibration curve was created. Then, a control serum Aqueck-Type II manufactured by Sumitomo Seiyaku Biomedical Co., Ltd., was determined.

Figure 2:
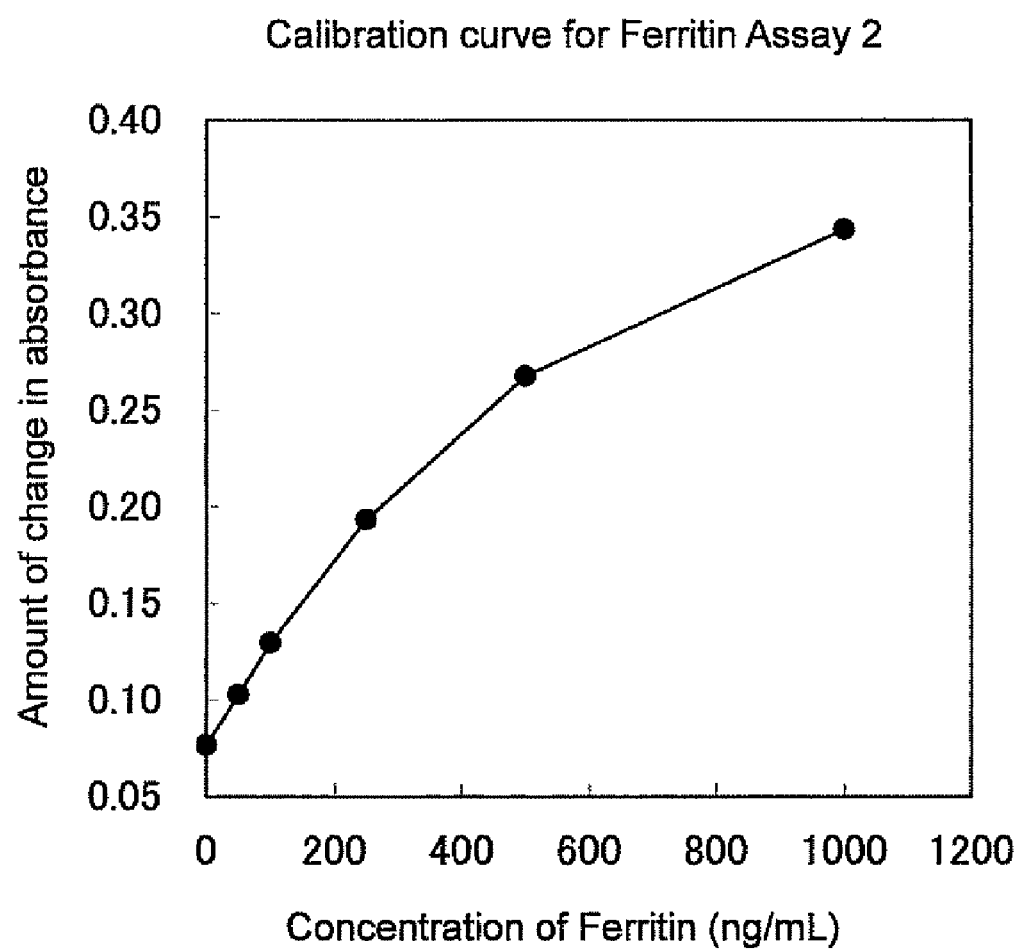
FIG. 2 is a graph showing the relationship between the concentration of ferritin and the amount of change in absorbance in Ferritin Assay 2, wherein the graph represents a calibration curve for Ferritin Assay 2.

Determination method: First, 160 µL of the first reagent was added to 10 µL of a sample, and the mixture was warmed at 37° C. for about 5 minutes. After warming, 80 µL of the second reagent was added and allowed to react at 37° C., and the amount of change in absorbance was measured by a Hitachi 7070 automatic analyzer at photometric points from 18 to 31 at wavelengths of 505 nm and 660 nm. FIG. 2 shows the calibration curve, and Table 2 shows the results of the determination of the control serum Aqueck-Type II.

TABLE 2

| Control serum (Indicated value: ng/mL) | Ferritin measured value (ng/mL) | |
|---|---|---|
| | First measurment | Second measurement |
| Low (50-67) | 55 | 56 |
| High (318-560) | 432 | 438 |

As shown by the calibration curve in FIG. 2, the amount of change in absorbance due to the agglutination reaction was increased depending on the concentration of the analyte ferritin. In other words, it can be seen that the amount of ferritin, which is the analyte contained in the sample, can be quantified by measuring the amount of change in absorbance due to the agglutination reaction and performing a comparison with the calibration curve. The results of the determination of the ferritin concentration shown in Table 2 were within the ranges of the indicated values for the amount of ferritin in the control serum Aqueck-Type II, and the accuracy of the present determination method was confirmed.

Example 8

Preparation of First Reagent for Haloperidol Assay

A first reagent for Haloperidol Assay was prepared by adding 3 µg/mL of a rabbit anti-haloperidol polyclonal antibody (see Japanese Laid-Open Patent Publication No. 2004-325192) and about 2.0 to 3.5 w/v % of polyethylene glycol serving as a reaction accelerator to the solution B.

Example 9

Preparation of Second Reagent for Haloperidol Assay

A second reagent for Haloperidol Assay was prepared by adding 140 mL of solution A and 35 µL of a haloperidol-bound bovine serum albumin solution (30 ng/mL, see Japanese Laid-Open Patent Publication No. 2004-325192) to 70 mL of a mouse anti-rabbit IgG-Fc monoclonal antibody-bound colloidal gold solution as prepared in Example 5.

Example 10

Haloperidol Assay

Figure 3:
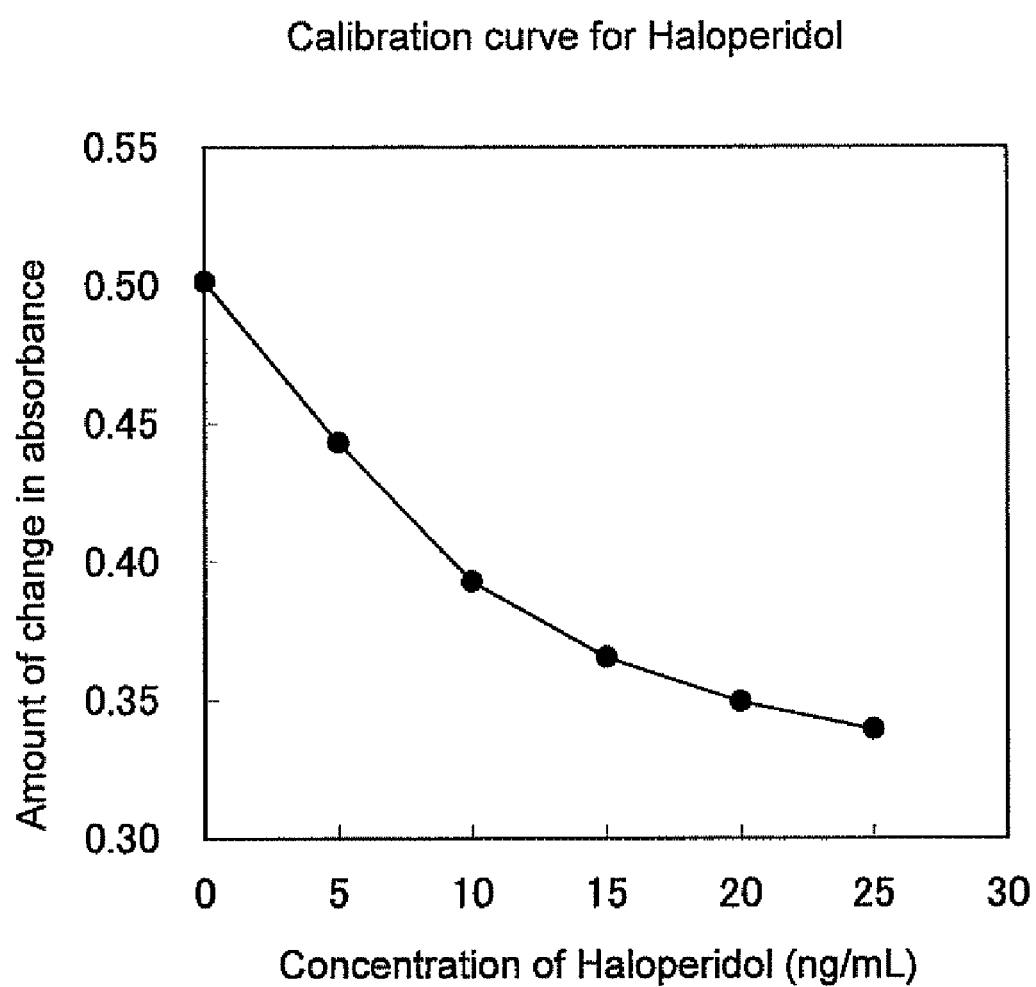
FIG. 3 is a calibration curve for haloperidol graphically showing the relationship between the concentration of haloperidol and the amount of change in absorbance.

In this example, the first reagent for Haloperidol Assay prepared in Example 8 was used as the first reagent, and the second reagent for Haloperidol Assay prepared in Example 9 was used as the second reagent. Samples containing haloperidol dissolved in the solution C at the concentrations of 0, 5, 10, 15, 20, and 25 ng/mL, respectively, were prepared. Then, 200 µL of the first reagent was added to 10 µL each of the samples containing haloperidol, and the mixtures were warmed at 37° C. for about 5 minutes. After warming, 50 µL of the second reagent was added and allowed to react at 37° C., and the amount of change in absorbance was measured by a Hitachi 7070 automatic analyzer at photometric points from 18 to 31 at wavelengths of 546 nm and 660 nm. FIG. 3 shows the relationship between the concentration of haloperidol and the amount of change in absorbance.

As shown in FIG. 3, the amount of change in absorbance due to the agglutination reaction was changed depending on the concentration of the analyte haloperidol. In other words, it can be found that the amount of haloperidol, which is the analyte contained in the sample, can be quantified by measuring the amount of change in absorbance due to the agglutination reaction and performing a comparison with a calibration curve.

According to the present invention, when a specific site recognized by the second specific binding substance is set to be a common region to first specific binding substances, various analytes can be easily determined simply by changing only the first specific binding substances (e.g., antibodies against the analytes) in accordance with the analytes. That is to say, the second specific binding substance can be commonly used in determination of various analytes, so that there is no need to perform the complicated operation for preparing the bound microparticles by binding different substances with respect to different analytes, and this also leads to a reduced cost.

Furthermore, according to the present invention, the substance (the first specific binding substance) that directly binds to the analyte is not bound to the microparticles of latex, gold colloid, or the like, so that the uncertainties due to binding with the microparticles, such as the change in the specificity of the first specific binding substance, the ability to bind to the analyte of the first specific binding substance, the possibility of autoagglutination, and the change in the stability of the first specific binding substance, are eliminated, and more precise determination can be achieved.

Moreover, the present invention does not require the B/F separation and is therefore also very suitable for automation. For example, when an automatic analyzer that is in widespread use in the clinical laboratory test field is used, all that is required is to change the first specific binding substances in accordance with the analytes, as described above, so that the present invention can also contribute to the labor saving. Therefore, the present invention is suitable as an immunoassay of a trace constituent using an antigen-antibody reaction for use in the industrial, environmental, and clinical laboratory test fields.

The invention claimed is:

1. A method for determining an analyte in a sample, comprising:
   (a) mixing the sample and a first specific binding substance, the first specific binding substance being a substance that can specifically bind to the analyte, to form a complex of the analyte in the sample and the first specific binding substance;
   (b) adding microparticles having a second specific binding substance bound thereto to a mixture obtained in the step (a) and mixing therewith, the second specific binding substance being a substance that can specifically bind to the first specific binding substance; and
   (c) determining the extent of an agglutination reaction of the microparticles, in a mixture obtained in the step (b), thereby determining the amount of analyte in the sample,
   wherein the second specific binding substance is a monoclonal antibody against the first specific binding substance and
   wherein the extent of agglutination of the microparticles increases with an increase in the amount of analyte in a sample such that the extent of agglutination of the microparticles relates to the amount of analyte in a sample.

2. A method for determining an analyte in a sample, comprising:
   (a) mixing the sample and a first specific binding substance, the first specific binding substance being a substance that can specifically bind to the analyte, to form a complex of the analyte in the sample and the first specific binding substance;
   (b) adding microparticles having a second specific binding substance bound thereto and an analyte-bound carrier to a mixture obtained in the step (a) and mixing therewith, the second specific binding substance being a substance that can specifically bind to the first specific binding substance, the analyte-bound carrier being a carrier to which a plurality of analytes or a plurality of sites of the analytes that are recognized by the first specific binding substance are bound; and
   (c) determining the extent of an agglutination reaction of the microparticles, in a mixture obtained in the step (b), thereby determining the amount of analyte in the sample,
   wherein the second specific binding substance is a monoclonal antibody against the first specific binding substance and
   wherein the extent of agglutination of the microparticles increases with an increase in the amount of the first specific binding substance that is present after the step (a) and that does not bind to the analyte, which amount is defined by the amount of the analyte in the step (a), such that the extent of agglutination of the microparticles relates to the amount of analyte in a sample.

3. The method of claim 1, wherein the first specific binding substance is an antibody against the analyte.

4. The method of claim 1, wherein the microparticles are of latex or gold colloid.

5. The method of claim 2, wherein the first specific binding substance is an antibody against the analyte.

6. The method of claim 2, wherein the microparticles are of latex or gold colloid.

7. The method of claim 3, wherein the microparticles are of latex or gold colloid.

8. The method of claim 5, wherein the microparticles are of latex or gold colloid.

* * * * *